United States Patent [19]

Miller et al.

[11] Patent Number: 4,737,504
[45] Date of Patent: Apr. 12, 1988

[54] 5-FLUORO-AND 8-FLUORO-TRIMETOQUINOL COMPOUNDS AND THE PROCESSES FOR THEIR PREPARATION

[75] Inventors: Duane D. Miller, Worthington; Dennis R. Feller, Columbus, both of Ohio; Michael T. Clark, West Chester, Pa.; Adeboye Adejare, Kensington, Md.; Karl J. Romstedt; Gamal Shams, both of Columbus, Ohio

[73] Assignee: Ohio State University Research Foundation, Columbus, Ohio

[21] Appl. No.: 890,490

[22] Filed: Jul. 25, 1986

[51] Int. Cl.$^4$ ..................... A61K 31/47; C07D 217/20
[52] U.S. Cl. .................................. 514/307; 546/149; 558/410; 564/366
[58] Field of Search .................. 546/149; 514/307

[56] References Cited
PUBLICATIONS

Yamada, et al., "Chemical Abstracts", vol. 96, 1982, col. 96:85389p.
Clark, et al., "Chemical Abstracts", vol. 106, 1987, col. 106:49995z.
Kirk et al., *J. Med. Chem.*, 22, 1493 (1979).
Miller et al., *J. Med. Chem.*, 19:763–766 (1976).
(List continued on next page.)

Primary Examiner—Glennon H. Hollrah
Assistant Examiner—James H. Turnipseed
Attorney, Agent, or Firm—Emch, Schaffer, Schaub & Porcello Co.

[57] ABSTRACT

The present invention relates to novel 5-fluoro- and 8-fluoro-trimetoquinol compounds of the general formula I wherein $X_1=F, X_2=H$ or $X_1=H, X_2=F$

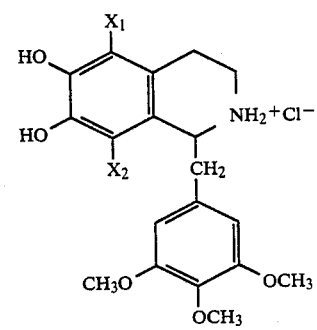

The present invention also relates to a process for making the 5-fluoro- and 8-fluoro-trimetoquinol compounds by condensation of an appropriately substituted phenethylamine to afford an appropriately substituted phenethylacetamide compound. The amides are cyclized to give appropriately substituted intermediate dihydroisoquinolines. Without isolation, the dihydroisoquinolines are reduced to give appropriately substituted tetrahydroisoqinolines. The hydrochloride salts of tetrahydroisoqinolines are prepared and subjected to hydrogenolysis, to give the fluorine substituted trimetoquinol compounds of the present invention. The present invention also encompasses the preparation of the phenethylamines by reducing appropriately substituted benzylcyanides and to the preparation of an intermediate benzylcyanide compound by converting a fluorine substituted methoxyphenol compound, under aminomethylation conditions into a N, N-dimethyl-4-hydroxy-3-methoxy-5-fluorobenzylamine. The benzylamine is converted to benzylnitrile and a functional group shuffle is carried out which yields the appropriately substituted benzylcyanide compound. In a composition aspect, the present invention encompasses novel pharmaceutical compositions comprising a compound of the formula I, together with a physiologically acceptable carrier or excipient, in an amount sufficient to increase $\beta_2$-adrenergic and antithrombotic activities while simultaneously decreasing the $\beta_1$-adrenergic activity in mammals, including humans. The compounds of the invention are useful in the treatment of pulmonary, cardiovascular or thromboembolic disorders.

10 Claims, 5 Drawing Sheets

OTHER PUBLICATIONS

Osei-Gyimah et al., *J. Med. Chem.*, 21:1173–1178 (1978).
Piascik et al., *Biochem. Pharmacol.*, 28:1807–1810 (1979).
Piascik et al., *Life Sci.*, 24:2433–2440 (1979).
Mukhopadhyay et al., *Eur. J. Pharmacol.*, 77:209–211 (1982).
Mukhopadhyay et al., *J. Pharmacol. Exp.*, 231:1–9 (1985).
Kirk et al., *Science*, 204, 1217 (1979).
Kirk-Othmer: Encyclopedia of Chemical Technology, vol. 2, Third Edition, copyright 1978 by John Wiley & Sons, Inc.

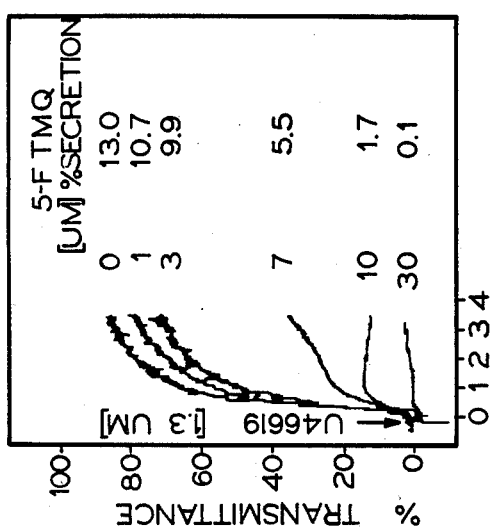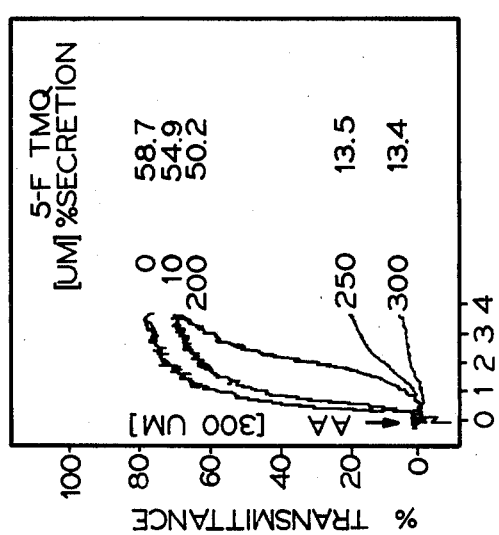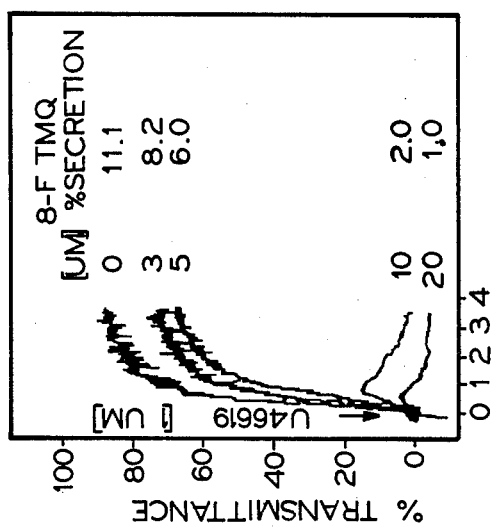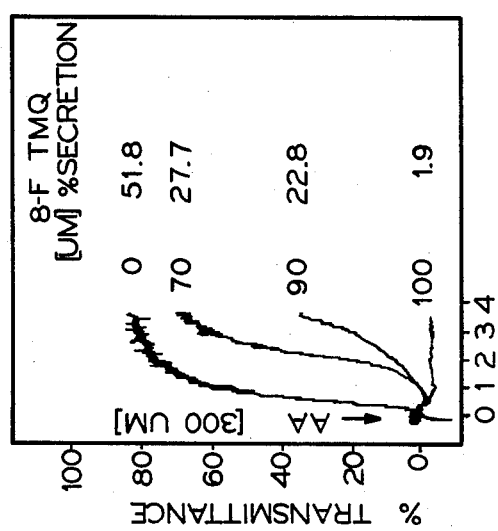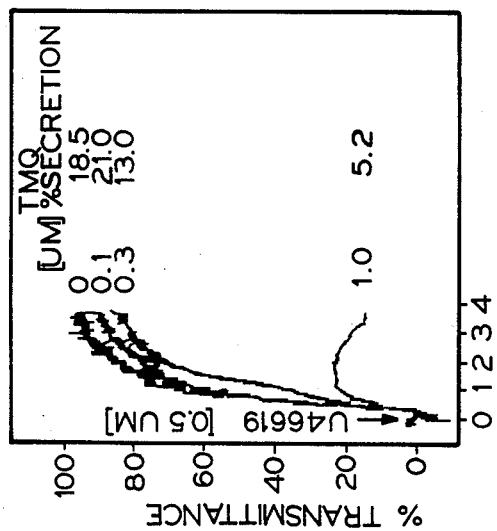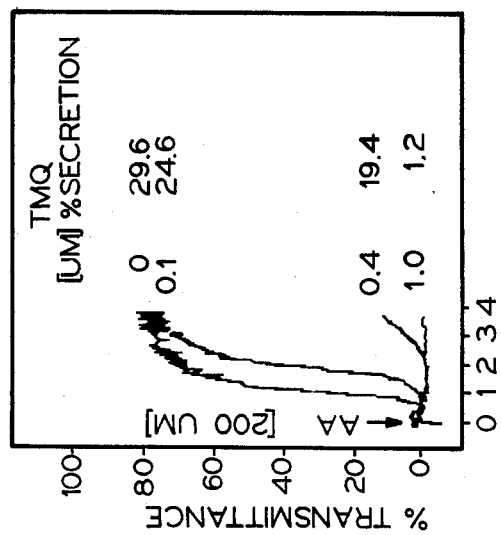

5-FLUORO- AND 8-FLUORO-TRIMETOQUINOL COMPOUNDS AND THE PROCESSES FOR THEIR PREPARATION

BACKGROUND OF THE INVENTION

The present invention relates generally to 5-fluoro- and 8-fluoro-trimetoquinol compounds and the processes for their manufacture, and pharmaceutical preparations thereof.

The invention further relates to the use of such compounds to increase the $\beta_2$-adrenergic activity while simultaneously decreasing the $\beta_1$-adrenergic activity in mammals, including humans. The invention further relates to the pharmaceutical use of such compounds in the treatment of pulmonary and cardiovascular diseases. In particular, the compounds of the invention are useful in the treatment of lower respiratory tract disorders, such as for example, asthma, allergen-induced bronchospasms or emphysema, or for the treatment of hypertension, or for the treatment of thromboembolic disorders.

The adrenergic nervous system is one portion of the autonomic nervous system, which regulates or controls the so-called vegetative or involuntary functions of the body. This nervous system innervates the major organs of the body, eg., the lungs and heart. The neurotransmitters released by the nerve terminals interact with receptors in the tissue of the various organs of the body to produce specific biological responses. The primary receptors upon which adrenergic stimulants act, have been divided into the $\alpha$- and $\beta$-adrenergic receptors. The $\beta$-receptors are associated with smooth muscle relaxation in the lower respiratory tract, relaxation of blood vessels in skeletal muscle, cardiac muscle stimulation, and lipolysis. The receptors associated with $\beta$-responses have been further classified as $\beta_1$ (cardiac stimulation and lipolysis) or $\beta_2$ (bronchodilation and vasodilation). There has been considerable effort to develop selective $\beta_2$ adrenergic stimulants. Such compounds would retain the important bronchodilation activity while being devoid of the cardiovascular, gastrointestinal, and central nervous system side effects produced by compounds possessing significant $\alpha$- and $\beta_1$-adrenergic receptor stimulation.

One adrenergic stimulant used extensively in the therapy of asthma has been isoproterenol. In the past, isoproterenol was popular because of its prompt and intense action in bringing about bronchodilation after inhalation. Unfortunately isoproterenol possesses little tissue selectivity and stimulates both $\beta_1$- and $\beta_2$-adrenergic receptors. The stimulation of the myocardium may lead to undesirable tachycardia, increase in cardiac output and an elevation in blood pressure. Since isoproterenol dilates previously constricted blood vessels in the lung, exaggerated ventilation blood flow inequality may result in a worsening hypoxia. Although isoproterenol has a fast onset of action (2-5 min), and a relatively short duration of action (averaging 1.5-2 h), some patients may become tolerant to its action. Excessive use of pressurized aerosols containing isoproterenol can not only lead to tolerance but may also be associated with an increase in deaths due to excessive $\beta_1$-stimulation of the heart.

Another well-known adrenergic stimulant is epinephrine which was the earliest catecholamine to be used for its bronchodilation activity. Epinephrine stimulates both $\alpha$- and $\beta$-adrenergic receptors to about the same degree. There are differences in the biological activity of the optical isomers of a number of adrenergic drugs closely related to epinephrine. R-(−)-epinephrine, the naturally occurring form, is more active than S-(+)-epinephrine on both $\alpha$- and $\beta$-adrenergic receptors. R-(−)-epinephrine, which can be extracted from adrenal glands is the isomer used as a drug. Epinephrine can also be synthesized wherein racemic epinephrine is resolved using (+)-tartaric acid to give R-(−)-epinephrine. Epinephrine is similar to isoproterenol in that it does not show selectivity in activating $\beta$-adrenergic receptors. Because of this nonselectivity and its ability to activate $\alpha$-adrenergic receptors, epinephrine may produce a variety of side effects including tachycardia, elevated blood pressure, headache, and tremors.

Modifications of epinephrine have been carried out in an attempt to produce a selective $\beta$-adrenergic agonist; for example, Kirk et al., in *J. Med. Chem.*, 22: 1493, 1979, reported that fluorine substitution at the 2-position of norepinephrine produces a selective $\beta$-adrenergic agonist, while the 6-fluoro analog of norepinephrine produces a selective $\beta$-adrenergic agonist. However, the corresponding 2-fluoro and 6-fluoro-dopamine analogs do not show selectivity for adrenergic receptors.

Another adrenergic stimulant is trimetoquinol 1, a bronchoselective $\beta$-adrenoceptor agonist of the tetrahydroisoquinoline class, which is useful for the treatment of moderate bronchial asthma.

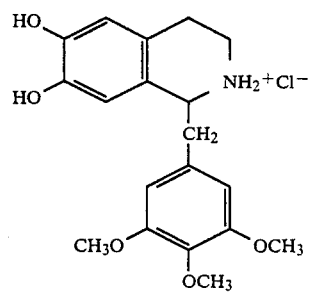

In addition to $\beta$-adrenoceptor activity, trimetoquinol 1 blocks endoperoxide/thromboxane arachidonic acid-mediated in vitro aggregation of human platelets. The S(−)-isomer of trimetoquinol is marketed in Japan as a bronchodilator for the treatment of asthma. However, the trimetoquinol 1 has the undesirable effect of also increasing the $\beta_1$-adrenergic activity which stimulates the heart.

Certain trimetoquinol analogs are described as having been prepared in Miller et al., *J. Med. Chem.*, 19: 763-766, 1976; Osei-Gyimah et al., *J. Med. Chem.*, 21: 1173-1178, 1978; Piascik et al., *Biochem. Pharmacol.*, 28: 1807-1810, 1979, and *Life Sci.*, 24: 2433-2440, 1979; Mukhopadhyay et al., *Eur. J. Pharmacol.*, 77: 209-219, 1982; and Mukhopadhyay et al., *J. Pharmacol. Exp. Ther.*, 232: 1-9, 1985; in an attempt to obtain more potent and organ selective $\beta$-adrenoceptor agents.

Although much effort has been made to provide an orally active, direct acting $\beta_2$-adrenergic agonist with rapid onset and long duration of action, literature contains no references to fluorine substituted trimetoquinol analogs, and until now no attempt has been made to substitute fluorine on the catechol segment of trimetoquinol in order to separate $\beta_2$- from $\beta_1$-adrenergic activity.

BRIEF DESCRIPTION OF THE DRAWING

FIGS. 6, 7 and 8 are a series of graphs showing the comparative effects of trimetoquinol (TMQ), 8-fluoro-trimetoquinol analog (8-F-TMQ) and 5-fluoro-trimetoquinol analog (5-F-TMQ), respectively, as inhibitors of U46619-induced human platelet aggregation and serotonin secretion.

FIGS. 9, 10 and 11 are a series of graphs showing the comparative effects of trimetoquinol (TMQ), 8-fluoro-trimetoquinol analog (8-F-TMQ) and 5-fluoro-trimetoquinol analog (5-F-TMQ), respectively, as inhibitors of arachidonic acid (AA)-induced human platelet aggregation and serotonin secretion.

FIGS. 14, 16 and 17 are a series of graphs showing the comparative effects of trimetoquinol (TMQ), 8-fluoro-trimetoquinol analog (8-F-TMQ) and 5-fluoro-trimetoquinol analog (5-F-TMQ), respectively, as inhibitors of adenosine diphosphate (ADP)-induced human platelet aggregation and serotonin secretion.

SUMMARY OF THE INVENTION

Figure 1:
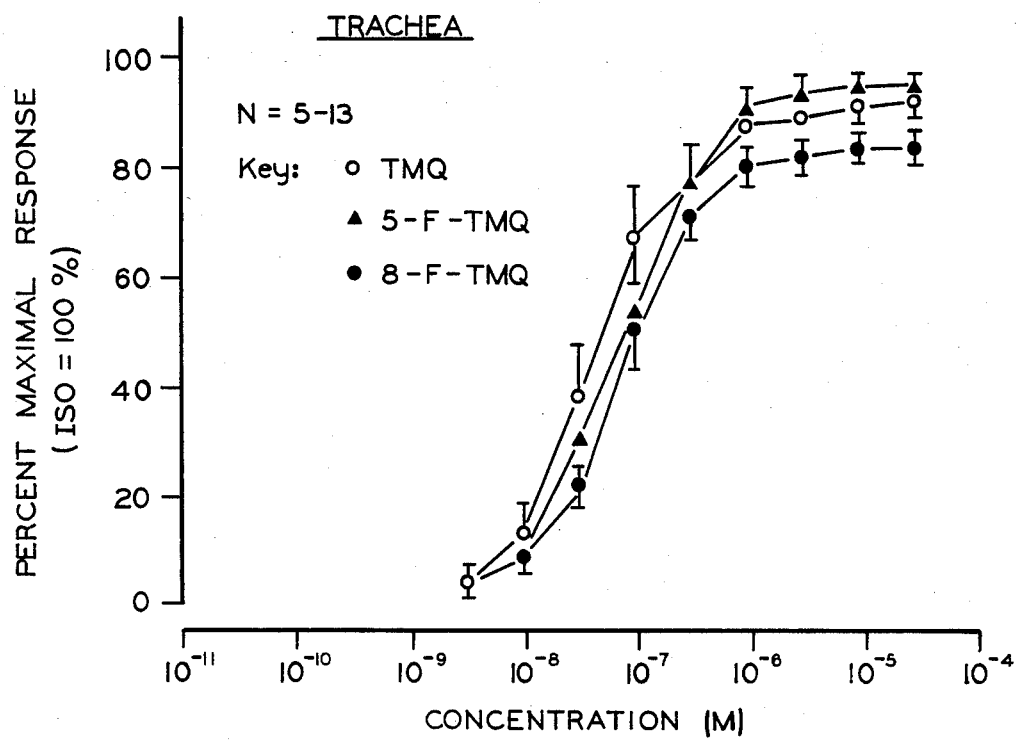
FIG. 1 is a graph showing comparative concentration-response curves of drug-induced relaxations of carbachol-contracted guinea pig trachea in the presence of trimetoquinol (TMQ), 5-fluoro-trimetoquinol analog (5-F-TMQ) and 8-fluoro-trimetoquinol analog (8-F-TMQ).

One aspect of the present invention relates to novel 5-fluoro- and 8-fluoro-trimetoquinol compounds of the general formula I wherein $X_1=F$, $X_2=H$ or $X_1=H$, $X_2=F$

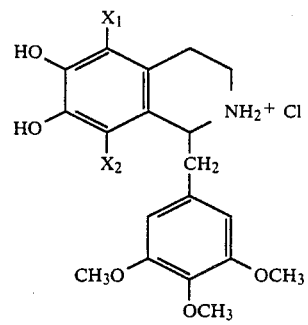

Another aspect of the present invention relates to a process for making the 5-fluoro- and 8-fluoro-trimetoquinol compounds by condensation of an appropriately substituted phenethylamine with trimethoxyphenylacetic acid to afford an appropriately substituted phenethylacetamide compound. The amides are cyclized to give appropriately substituted intermediate dihydroisoquinolines. Without isolation, the dihydroisoquinolines are reduced to give appropriately substituted tetrahydroisoquinolines. The hydrochloride salts of tetrahydroisoquinolines are prepared and subjected to hydrogenolysis, to give the fluorine substituted trimetoquinol compounds of the present invention.

The present invention also encompasses the preparation of the phenethylamines by reducing appropriately substituted benzylcyanides, and the preparation of an intermediate benzylcyanide compound by converting a fluorine substituted methoxyphenol compound, under aminomethylation conditions into 5-fluorobenzylamine. The benzylamine is converted to benzylnitrile and functional group shuffle is carried out, which yields the appropriately substituted benzylcyanide compound.

In a composition aspect, the present invention encompasses novel pharmaceutical compositions comprising a compound of the formula I, together with a physiologically acceptable carrier or excipient, in an amount sufficient to increase $\beta_2$-adrenergic and antithrombotic activities while simultaneously decreasing the $\beta_1$-adrenergic activity in mammals, including humans. The compounds of the invention are useful in the treatment of pulmonary, cardiovascular and thromboembolic disorders.

DESCRIPTION OF INVENTION

The invention provides compounds of the general formula I

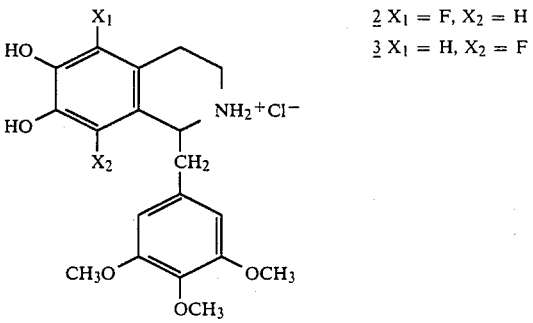

$\underline{2}$ $X_1 = F$, $X_2 = H$
$\underline{3}$ $X_1 = H$, $X_2 = F$ wherein $X_1=F$, $X_2=H$; and wherein $X_1=H$, $X_2=F$. The compounds of the general formula I above possess selective and potent $\beta_2$-adrenergic agonist activity while having minimum $\beta_1$-adrenergic agonist activity. The invention also provides processes for the preparation of compounds of the general formula I above. The invention also provides for compositions comprising compounds of the general formula I above, and the physiologically acceptable salts thereof. The 5-fluoro- (2) and 8-fluoro- (3) trimetoquinol compounds of the present invention and their salts are useful in the treatment of pulmonary and cardiovascular diseases.

The compounds of the invention are particularly useful in the treatment of lower respiratory tract disorders, such as asthma, allergen-induced bronchospasms and emphysema. The compounds of the invention are also particularly useful in the treatment of hypertensive or cardiovascular disorders. The invention accordingly further provides compounds of general formula I and their physiologically acceptable salts in the form of pharmaceutical preparations which contain them in association with a compatible pharmaceutical carrier or excipient material.

Suitable physiologically acceptable salts are the acid addition salts formed with inorganic acids, for example, hydrochlorides, hydrobromides, phosphates and sulfates; and with organic acids, for example, citrates, tartrates, acetates, maleates and succinates. The hydrochlorides are particularly useful.

The compounds according to the invention may be formulated in a conventional manner, optionally together with one or more other active ingredient, for administration by any convenient route. For example, the pharmaceutical compositions may take the form of an aerosol inhalant, a solution inhalant, tablets or injections. A proposed dosage to relieve bronchoconstriction in asthma in man, for example, is 0.5 ml of a 0.5% solution. The precise doses administered will of course depend on the age and medical condition of the patient.

The 5-fluoro- and 8-fluoro-analogs of trimetoquinol can be manufactured in accordance with the invention by condensation of the appropriately substituted phenethylamine compounds of the formula 4 or 5, respectively,

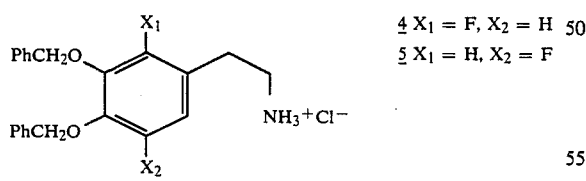

$\underline{4}$ $X_1 = F, X_2 = H$
$\underline{5}$ $X_1 = H, X_2 = F$ with trimethoxyphenylacetic acid of the formula 6

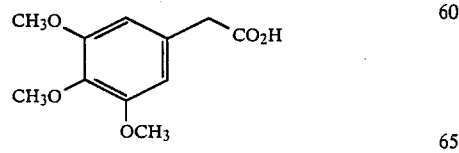

to afford the phenethylacetamide compounds of the formula 7 or 8, respectively;

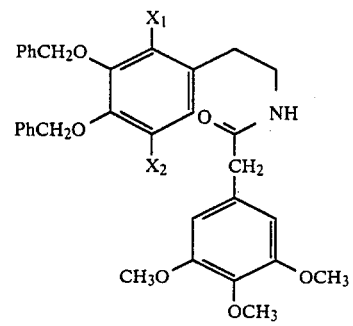

$\underline{7}$ $X_1 = F, X_2 = H$
$\underline{8}$ $X_1 = H, X_2 = F$

The phenethylacetamide compounds of the formula 7 or 8, are cyclized under Bischler-Napieralski conditions using POCl$_3$ in toluene to give the intermediate dihydroisoquinoline compounds. Without isolation, the dihydroisoquinoline compounds are reduced with NaBH$_4$ to give the tetrahydroisoquinoline compounds of the formula 9 or 10, respectively;

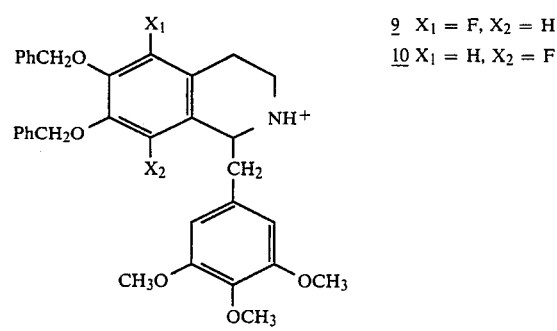

$\underline{9}$ $X_1 = F, X_2 = H$
$\underline{10}$ $X_1 = H, X_2 = F$

The hydrochloride salts of the tetrahydroisoquinoline compounds of the formula, 9 or 10 are prepared and subjected to hydrogenolysis to give the catechol compounds of the formula 2 or 3, respectively;

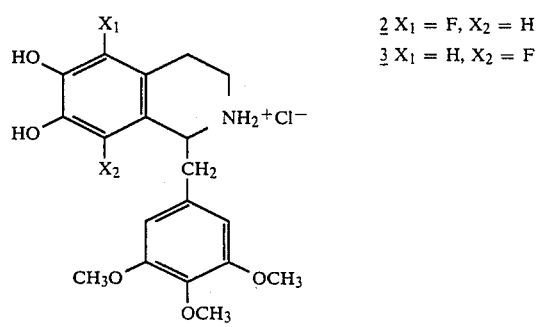

$\underline{2}$ $X_1 = F, X_2 = H$
$\underline{3}$ $X_1 = H, X_2 = F$

The phenethylamine compounds of the formula 4 or 5, above can be manufactured by reducing a benzylcyanide compound of the formula 11 or 12, respectively, by treatment with BH$_3$-THF to give the compounds of the formula 4 or 5, respectively.

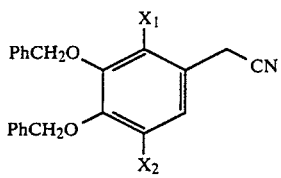

11 X₁ = F, X₂ = H
12 X₁ = H, X₂ = F

The intermediate benzylcyanide compound of the formula 12 above, according to the present invention, may be prepared by converting a 2-fluoro-6-methoxyphenol compound of the formula 13

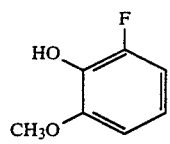

under aminomethylation conditions, with formaldehyde and N,N-dimethylamine, into the N,N-dimethyl-4-hydroxy-3-methoxy-5-fluorobenzylamine compound of the formula 14

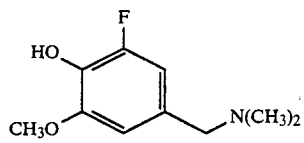

The benzylamine compound of the formula 14, by treatment with methyliodide and displacement with NaCN, is converted into the 3-methoxy-4-hydroxy-5-fluorobenzylnitrile compound of formula 15

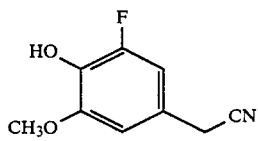

The benzylnitrile compound of the formula 15 is treated with BBr₃, followed by dibenzylation of the catechol 3,4-dihydroxy-5-fluorobenzylcyanide compound of the formula 16

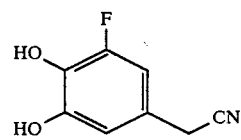

with benzylchloride to give the 3,4-dibenzyloxy-5-fluorobenzylcyanide compound of the formula 12

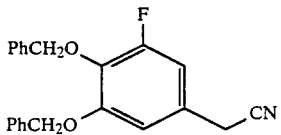

The intermediate benzylcyanide compound of the formula 11, above may be manufactured by preparing the nitrile compound of the formula 17

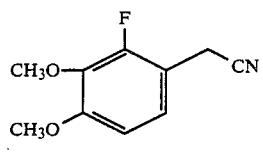

from 3-fluoroanisole in a manner similar to that described in Ladd et al., *J. Org. Chem.*, 46: 203, 1981, except that the phenol obtained from 3-fluoroanisole is distilled before methylation to give the 3-fluoroveratrole compound of the formula 18

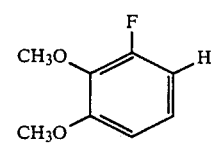

Halogenoalkylation (chloromethylation) of 3-fluoroveratrole gives the halide compound the formula 19

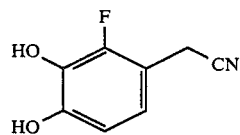

which is converted into the nitrile compound of the formula 17 above, with sodium cyanide. Both the halide compound of the formula 19 and the nitrile compound of the formula 17 can be purified by flash chromatography using 20 and 25% ethyl acetate/hexane solutions, respectively, for elution.

The benzylnitrile compound of the formula 17 is demethylated by treatment with BBr₃, followed by dibenzylation of the catechol 3,4-dihydroxy-2-fluorobenzylcyanide compound of the formula 20

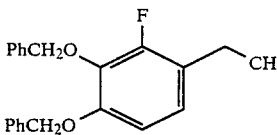

with benzylchloride to give the 3,4-dibenzyloxy-2-fluorobenzylcyanide compound of the formula 11

Structural requirements for optimal β-adrenoceptor activity of trimetoquinol 1 include the catechol moiety, amino nitrogen and 1-benzyl substituent. In contrast to previous work which suggested that the changes in α- and β-adrenoceptor activities of 2- or 6-fluorine substituted norepinephrine were due to an interaction between the aromatic ring and the side chain containing the β-hydroxy group, fluorine addition to 1 did not produce a dramatic effect on the conformation since the phenethylamine segment is contained within the tetrahydroisoquinoline nucleus. Further, an interaction of fluorine atoms with the 1-benzyl substituent is unlikely since the steric bulk of fluorine is comparable to that of hydrogen. Rather, the presence of fluorine atoms in the catechol moiety, shows that electronic effects attributable to the fluorine atom may alter the acidity of adjacent phenolic groups. In this regard, the ionization of phenols is increased by the presence of fluorine atoms placed in adjacent positions, as shown in Table 1. The greatest effect on reduction of $\beta_1$-adrenoceptor activity is found with the 8-fluoro (3) analog. The relative ionization of the tetrahydroisoquinolines plays an important role in the interaction of these molecules with $\beta$-adrenoceptors, and in particular $\beta_1$-adrenoceptor tissues. The 5-fluoro (2) analog is 4 times more acidic than 1 and is also about 4 times less active on $\beta_1$-adrenoceptors. In agreement with this observation, the 8-fluoro-(3) analog is 8 times more acidic than 1 and is 10 times less active on $\beta_1$-adrenoceptors. Taken together, the reduced potency on the $\beta_1$-adrenoceptor tissues is related to the relative degree of ionization of the tetrahydroisoquinolines.

The 5-fluoro (2) and 8-fluoro (3) analogs of the present invention maintain potency for stimulation of $\beta_2$-adrenoceptors, but not of $\beta_1$-adrenoceptors. These changes in $\beta_2/\beta_1$-selectivity are due to the electronic influence of fluorine and its effect on ionization of the phenolic groups and the binding of the catechol segment of 1 to $\beta_1$- and $\beta_2$-adrenoceptors.

TABLE 1

| Ultraviolet Spectral and pK$_a$ Data for TMQ, 5-FTMQ and 8-FTMQ[a] | | | | | |
|---|---|---|---|---|---|
| Compound | Solvent[b] | $\lambda_{max}$ ($\epsilon$) | Solvent[c] | $\lambda_{max}$ ($\epsilon$) | pK$_a$ |
| TMQ | A | 280(15,000) | B | 298(15,000) | 8.77 ± 0.15 |
| 5-FTMQ | A | 275(6,700) | B | 285(10,000) | 8.11 ± 0.15 |
| 8-FTMQ | A | 275(7,600) | B | 287(12,000) | 7.86 ± 0.15 |

[a]Spectra were measured on a Beckman DU-40 spectrophotometer.
[b]Solvent A, 0.1 M HCl.
[c]Solvent B, 0.1 M Tris(hydroxymethyl)aminomethane.

The $\beta_2/\beta_1$-adrenergic activity was determined using the following procedure: Male albino Hartley guinea pigs were employed in all experiments. The isolation and procedures for testing of each compound ($10^{-9}$ to $3 \times 10^{-5}$M) with isolated guinea pig atria and trachea were identical with those described by Sober et al., J. Med. Chem., 24: 970, 1981.

Male guinea pigs (Hartley strain, Glenn Carr, Columbus, OH) weighing between 400 and 700 grams were reserpinized (5 mg/kg, i.p.) 12–16 hours before experiments. Animals were sacrificed by a sharp blow to the head and the atria and trachea were quickly removed by standard procedures (The Staff, University of Edinburgh, "Pharmacological Experiments on Isolated Preparation", Livingston, London, pp. 104–111, 1970). Trachea were spirally cut into 2 to 4 matched strips (Constantine, J. Pharm. Pharmac., 17: 34–35, 1965). Spontaneously beating atria and tracheal strips were mounted in 10 ml tissue baths filled with Krebs-Heinsleit solution (millimolar concentrations: NaCl, 118; KCl, 4.7; CaCl$_2$-2H$_2$O, 2.5; MgCl$_2$-6H$_2$O, 5.0; NaH$_2$PO$_4$H$_2$O, 1.0; NaHCO$_3$, 2.5; and dextrose, 11) warmed to 37° C. and bubbled with 95% O$_2$:5% CO$_2$. Tensions of 1 and 3 gm were applied to the atria and trachea, respectively.

Following a 1 hour equilibration period, the $\beta_1$-adrenergic properties of the trimetoquinol analogs in spontaneously beating guinea pig right atria were analyzed by constructing cumulative concentration-response curves of the compounds according to the method of Van Rossum, Arch. Int. Pharmacodyn. Ther. 143: 299–330 (1963). Following completion of the concentration-response curve, the maximal chronotropic response of the tissue were elicited by a dose of $1 \times 10^{-5}$M isoproterenol (ISO). All trimetoquinol analog responses were expressed in terms of the ISO response.

In experiments where propranolol was used to demonstrate the $\beta$-adrenoceptor activities of trimetoquinol analogs, an initial concentration-response curve was constructed as above. Following a 1 hour wash, a selected concentration of propranolol was incubated with the tissue for 30 minutes prior to constructing a second concentration-response curve to the same trimetoquinol analog.

Preliminary experiments indicated that only one concentration-response curve could be obtained from each tracheal strip. Following a minimum 1 hour equilibration period, a concentration of $3 \times 10^{-7}$M carbachol was administered to the strips. This concentration was determined to induce a 60–70% maximal contraction in tracheal strips. From carbachol-induced baseline, cumulative concentration-response curves of the $\beta_2$-adrenergic (relaxant) actions of trimetoquinol analogs were constructed as described by Van Rossum, supra. A final dose of $1 \times 10^{-5}$M ISO was administered to each tissue to induce maximal relaxation and all trimetoquinol analog-induced responses were expressed in terms of the ISO response.

Each drug concentration was added only after the effects of the previous concentration reached a maximum and remained constant. The final maximum concentration of the testing compound did not increase the effect. Responses for agonists were expressed as pD$_2$ values ($-$log EC$_{50}$) values and were calculated directly from graphical plots of % maximal response versus log molar drug concentration. Other experiments were done in the presence of propranolol ($3 \times 10^{-8}$M), and the pK value of this antagonist was determined using the equation: $pK_B = -\log\ ([I]/CR - 1)$. Where CR=concentration ratio=EC$_{50}$ of drug (presence of propranolol)/EC$_{50}$ of drug (absence of propranolol) and [I]—molar concentration of propranolol, $3 \times 10^{-8}$M.

Phenol acidities (pKa) were determined spectrophotometrically, as described by Albert et al., "The determination of Ionization Constants" 3rd Ed., Chapman and Hall, London and New York, 1984, by measuring the absorption as a function of pH in tris(hydroxymethyl)aminomethane buffer. The spectral data of the neutral and ionized species are shown in Table 1. Since the catechols tended to oxidize in basic media the buffers were degassed and flushed with argon prior to use.

Figure 2:
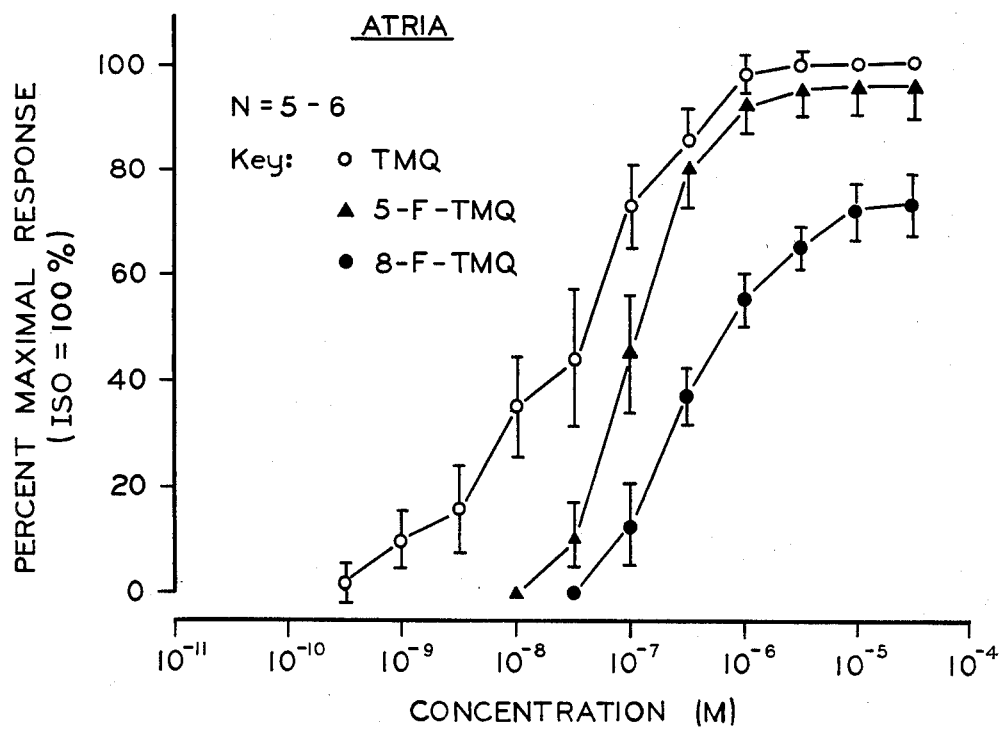
FIG. 2 is a graph showing comparative concentration-response curves of drug-induced chronotropy of guinea pig atria in the presence of trimetoquinol (TMQ), 5-fluoro-trimetoquinol analog (5-F-TMQ) and 8-fluoro-trimetoquinol analog (8-F-TMQ).

The concentration dependent effects of trimetoquinol (1), and the 5-fluoro (2) and 8-fluoro (3) analogs were evaluated using guinea pig tracheal strips and right atria as representative $\beta_2$- and $\beta_1$-adrenergic systems, as shown respectively in FIGS. 1 and 2. Each compound is nearly equally active as an agonist on tracheal relaxation. In contrast, the rank order of stimulatory potency for these compounds in atria is 1>2>3. Whereas 1 and 2 give similar maximal effects in both of these -adrenoceptor tissues, analog 3 is found to be a partial stimulant in atria.

Additional experiments were undertaken in the presence of propranolol to determine whether the 5-fluoro- (2) and 8-fluoro- (3) analogs produced their stimulatory effects by activation of β-adrenoceptors. The concentration response curves of analogs 2 and 3 were shifted to the right in a parallel fashion and the experimentally calculated $pK_B$ values of propranolol against each compound were nearly identical in atria and trachea as shown in Table 2. These concentration ratio shifts in the presence of propranolol are similar to that seen with trimetoquinol in these same β-adrenoceptor systems.

Data on the potency ratio for the fluorine analogs relative to 1 are given for each tissue system in Table 2, and show that the potencies of analogs 2 and 3 on $β_1$-adrenoceptors are reduced by about 4- and 10-fold, respectively. In contrast to 1, the results also show that each fluorinated analog is more potent as an agonists in the $β_2$-adrenoceptor. Accordingly, $β_2/β_1$-selectivity ratios of 2 and 3 were 4- and 8-fold greater, respectively, than the parent drug 1 and the rank order of $β_2/β_1$-selectivity was 3>2>1.

The biological results, as seen in Table 2 below, clearly demonstrate that the substitution of a fluorine atom at either the 5- or 8-position of the tetrahydroisoquinoline nucleus does not produce any major change in the stimulatory activity of the parent drug 1 on $β_2$-adrenoceptors. However, a progressive reduction in the activation of $β_1$-adrenoceptors is seen with 5-fluoro- and 8-fluoro-substitution, respectively. A reduced selectivity for $β_1$-adrenoceptors occurs by substitution of a fluorine atom for a hydrogen on the catechol ring system of 1.

aorta was excised, cleaned of any adhering fat and connecting tissue, spirally cut into 2 matched strips, Constantine, supra. (2.0×0.3 cm). Strips were mounted in 10 ml tissue baths filled with the physiological salt solution in which $3 \times 10^{-6}$M indomethaecin was present. A tension of 1 gm was applied to the strips. Responses of the tissues to drugs were monitored via Grass FT-03 isometric force transducers connected to a Grass Model 7C polygraph (Grass Instruments Co., Quincy, MA).

In experiments where the ability of the trimetoquinol analogs to antagonize U46619-induced contractions of rat thoracic aorta was evaluated, aortic strips were equilibrated for 1 hour in Krebs-Heinsleit solution containing $3 \times 10^{-6}$M indomethacin, pretreated with phenoxybenzamine (PBZ) for 30 minutes, washed for 15 minutes, and pretreated with sotalol for 15 minutes. Some experiments were done in the absence of indomethacin. Concentration-dependent responses to U46619 were constructed in each preparation as described by Van Rossum, supra. Following a 1 hour wash, antagonist pretreatments were again administered and supplemented with a selected concentration of each trimetoquinol analog 30 minutes prior to construction of a second concentration-response curve to U46619. Preliminary experiments indicated that no significant tissue desensitization (P<0.05) resulted from construction of a consecutive concentration-response curve to U46619 in the same preparation.

Effective concentration-50 ($EC_{50}$) values of the agonists were determined graphically from individual plots of percent response versus log concentration. The potency of each agonist was expressed as a $pD_2$ value where $pD_2$ is equal to the negative logarithm of the experimentally determined $EC_{50}$ value.

Antagonists were quantitated by calculating their $pK_B$ or $pA_2$ values according to the methods of Furchgott, Ann. N.Y. Acad. Sci., 139: 553–570 (1967) and Arunlakshana et al., Br. J. Pharmacol., 14: 48–58 (1959). The $pK_B$ value is equivalent to the −log of

TABLE 2

| | Comparison of Trimetoquinol (TMQ) and Fluorinated Analogs on $β_2$ (trachea) and $β_1$ (atria)-Adrenoceptors and Effect of Propranolol[a] | | | | | | | | |
|---|---|---|---|---|---|---|---|---|---|
| | Trachea $(β_2)$[b] | | | | Atria $(β_1)$[b] | | | | Selectivity Ratio[d] $(β_2/β_1)$ |
| Compound | $pD_2$ ± SEM | IAR ± SEM[c] | $pK_B$ ± SEM | Potency[d] Ratio | $pD_2$ ± SEM | IAR ± SEM[c] | $pK_B$ ± SEM | Potency[d] Ratio | |
| TMQ (1) | 7.24 ± 0.02 (5) | 0.95 ± 0.01 | — | 1.00 | 7.52 ± 0.21 (5) | 1.00 ± 0.0 | — | 1.00 | 1.0 |
| 5-F-TMQ (2) | 7.26 ± 0.11 (5) | 0.95 ± 0.01 | — | 1.05 | 6.95 ± 0.13 (6) | 0.96 ± 0.04 | — | 0.27 | 3.88 |
| 5-F-TMQ Plus $3 \times 10^{-8}$ propranolol | 6.38 ± 0.11 (4) | 0.98 ± 0.01 | 8.69 ± 0.13 | — | 5.95 ± 0.04 (4) | 1.00 ± 0.0 | 8.48 ± 0.04 | — | — |
| 8-F-TMQ (3) | 7.15 ± 0.14 (5) | 0.86 ± 0.02 | — | 0.81 | 6.53 ± 0.11 (5) | 0.74 ± 0.05 | — | 0.102 | 7.94 |
| 8-F-TMQ Plus $3 \times 10^{-8}$ propranolol | 5.38 ± 0.03 (4) | 0.91 ± 0.04 | 8.83 ± 0.01 | — | 5.55 ± 0.10 (4) | 0.66 ± 0.06 | 8.45 ± 0.11 | — | — |

[a]Drug concentrations used varied from $10^{-9}$ to $3 \times 10^{-5}$M. Concentration of propranolol was $3 \times 10^{-8}$M.
[b]Values are the mean ± SEM of N = 4–13 (numbers given in parentheses).
[c]IAR = Intrinsic activity ratio = ratio of maximal drug effect to maximal response of TMQ.
[d]Potency Ratio = $EC_{50}$ (trimetoquinol)/$EC_{50}$ (drug).
[e]Selectivity Ratio = Potency Ratio $(β_2)$/Potency Ratio $(β_1)$ for each drug.

The vasoconstrictive activity of U46619 (a stable thromboxane $A_2$ agonist) on thoracic aorta tissue was determined as follows: Male Sprague-Dawley rats (Harlan Industries, Inc., Cumberland, IN) weighing between 250 and 350 gm were stunned and killed by cervical dislocation. A 2–3 cm segment of thoracic

Figure 3:
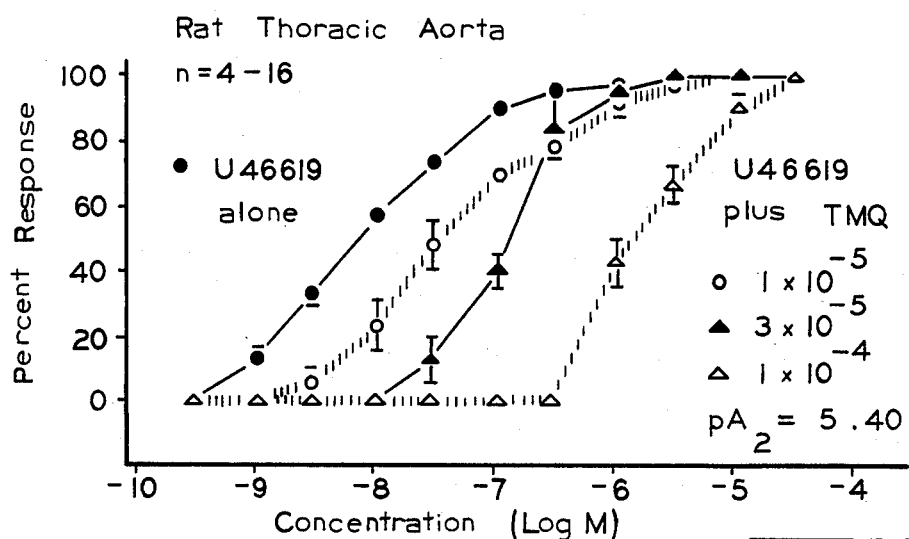
FIG. 3 is a graph showing comparative concentration-response curves of U46619-induced contractions of rat thoracic aorta in the presence of U46619 or U46619 plus varying concentrations of trimetoquinol (TMQ).
Figure 4:
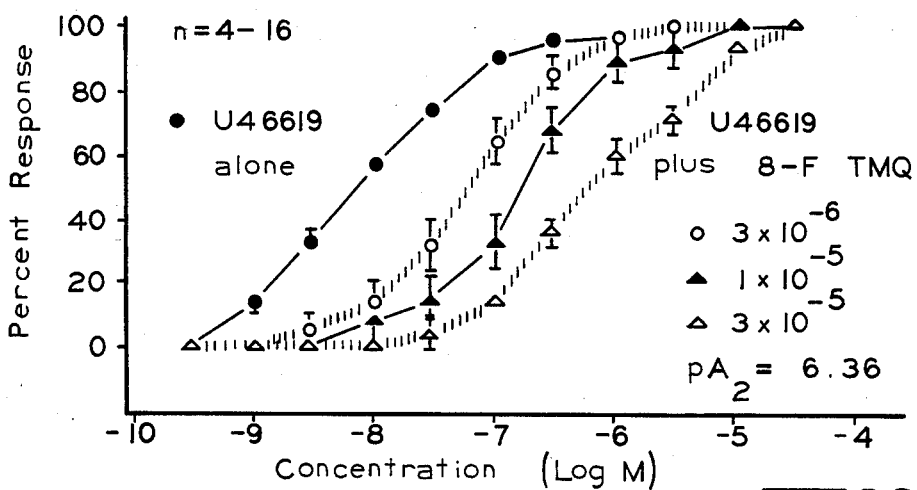
FIG. 4 is a graph showing comparative concentration-response curves of U46619-induced contractions of rat thoracic aorta in the presence of U46619 or U46619 plus varying concentrations of 8-fluoro-trimetoquinol (8-F-TMQ).
Figure 5:
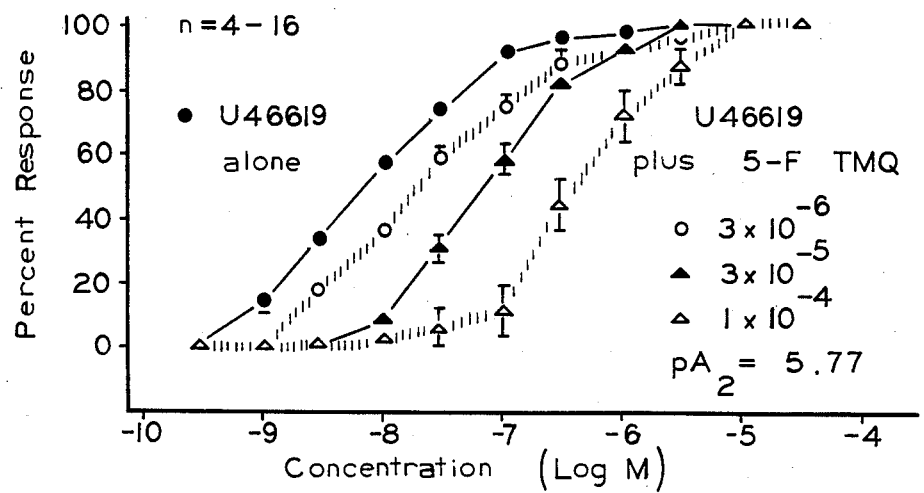
FIG. 5 is a graph showing comparative concentration-response curves of U46619-induced contractions of rat thoracic aorta in the presence of U46619 or U46619 plus varying concentrations of 5-fluoro-trimetoquinol (5-F-TMQ).
Figure 12:
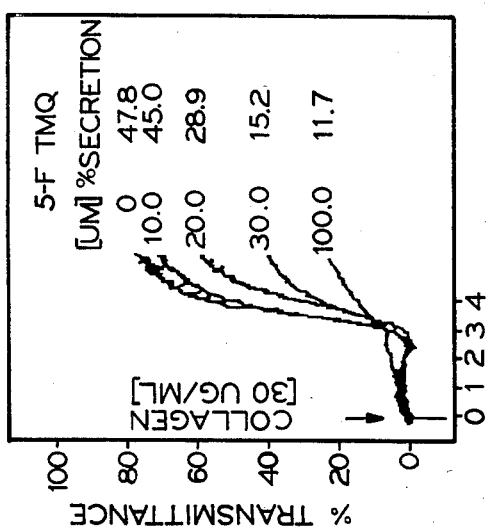
FIGS. 12, 13 and 14 are a series of graphs showing the comparative effects of trimetoquinol (TMQ), 8-fluoro-trimetoquinol analog (8-F-TMQ) and 5-fluoro-trimetoquinol analog (5-F-TMQ), respectively, as inhibitors of collagen-induced human platelet aggregation and serotonin secretion.
Figure 15:
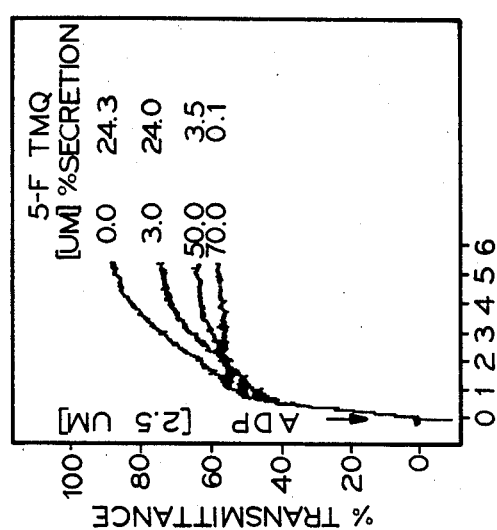
Figure 13:
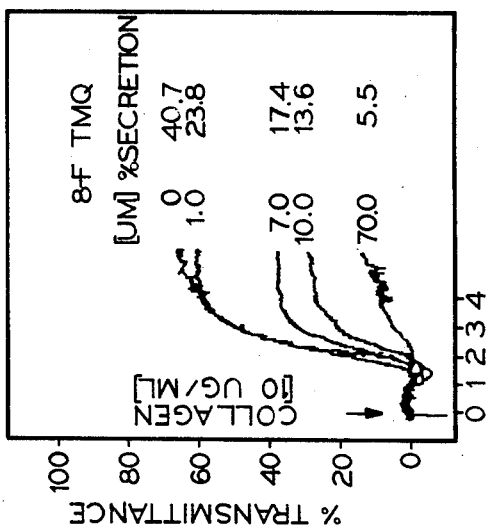
Figure 16:
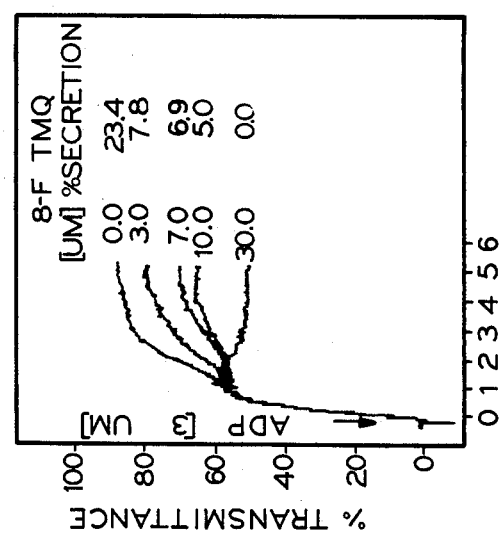
Figure 14:
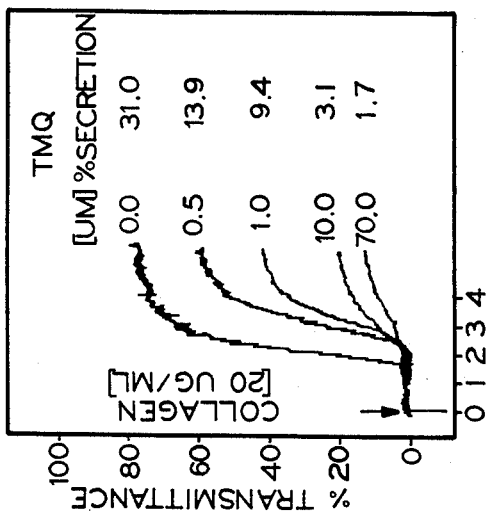
Figure 17:
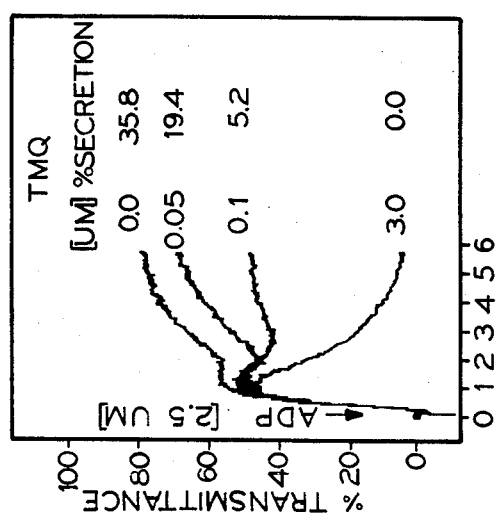
Figure 20:
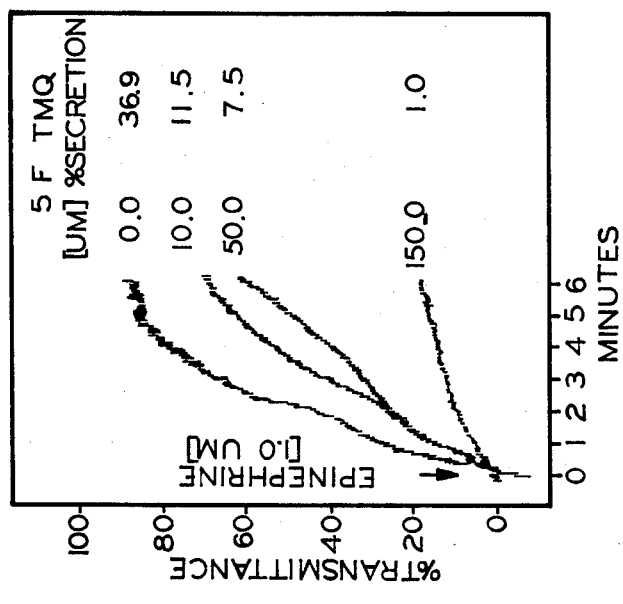
FIGS. 18, 19 and 20 are a series of graphs showing the comparative effects of trimetoquinol (TMQ), 8-fluoro-trimetoquinol analog (8-F-TMQ) and 5-fluoro-trimetoquinol analog (5-F-TMQ), respectively, as inhibitors of epinephrine-induced human platelet aggregation and serotonin secretion.
Figure 19:
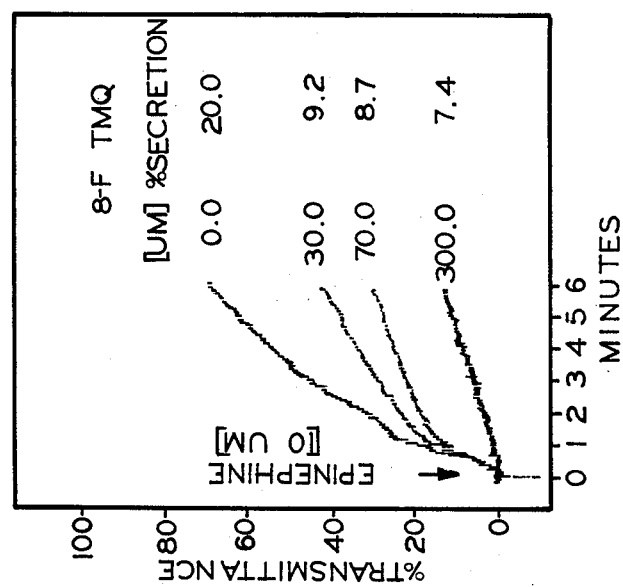
Figure 18:
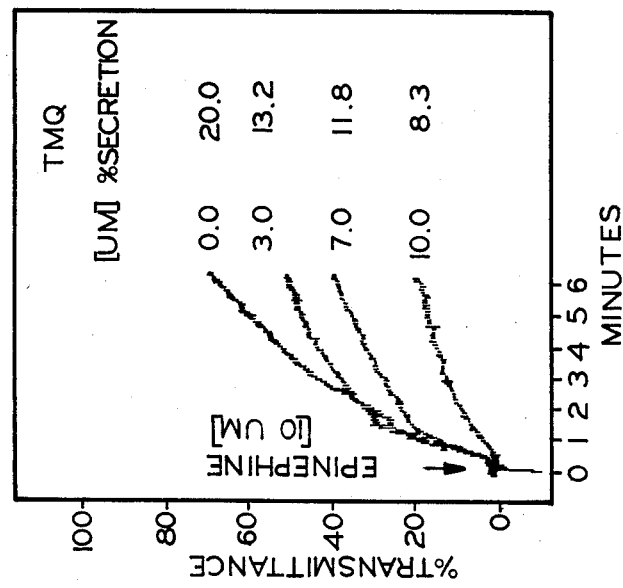

[I]/(CR−1), where $pK_B$ is the negative logarithm of the apparent dissociation constant of the antagonist ($K_B$), [I] is the concentration of the antagonist, and CR is the concentration ratio of the agonist $EC_{50}$ in the presence of antagonist to the agonist $EC_{50}$ in the absence of antagonist. To determine significant differences between $pD_2$, $pK_B$ or $pA_2$ values, a 5% level of significance was used. Arunlakshana plots were analyzed by computer according to the method of Tallarida et al., *Manual of Pharmacological Calculations With Computer Programs*, 29-31, (1981). The results, as shown in FIGS. 3, 4, and 5, are summarized in the following Tables 3 and 4. Data show that the inhibitory potencies of analogs 2 and 3 on U46619-induced contractions of rat thoracic aorta are about 2- and 10-fold greater than trimetoquinol (1). The biological results clearly demonstrate that substitution of a fluorine atom at either the 5- or 8-position of the tetrahydroisoquinoline nucleus produces drugs with increased anti-thromboxane $A_2$ (U46619) properties in vascular smooth muscle tissue.

TABLE 3

Concentration Dependent Inhibitory Effects of 5-Fluortrimetoquinol-(5-FLTMQ) Against U46619 in Rat Thoracic Aorta

| 5-FLTMQ Conc., M. | n | $pD_2{}^b$ | $\Delta pD_2{}^c$ | $pK_B \pm SEM^d$ |
|---|---|---|---|---|
| None | 16 | 8.17 ± 0.06 | — | — |
| $3 \times 10^{-6}$ | 4 | 7.69 ± 0.08$^e$ | 0.48 ± 0.07 | 5.82 ± 0.11 |
| $3 \times 10^{-5}$ | 12 | 7.14 ± 0.08$^e$ | 1.02 ± 0.08 | 5.50 ± 0.29 |
| $1 \times 10^{-4}$ | 4 | 6.40 ± 0.16$^e$ | 1.77 ± 0.16 | 5.76 ± 0.16 |

$^a$Values are the mean ± SEM of n = 4-16
$^b pD_2 = -\text{Log } ED_{50}$
$^c \Delta pD_2 = pD_2$ (control)-$pD_2$ (treatment)
$^d pK_B = -\text{Log } [A]/(CR-1)$ where [A] - molar concentration of analog and CR = concentration ratio = $EC_{50}$ (plus analog)/$EC_{50}$ (control)
$^e p < 0.05$ - significantly different from control

TABLE 4

Concentration Dependent Inhibitory Effect of 8-Fluorotrimetoquinol (8-FLTMQ) Against U44619 in Rat Thoracic Aorta

| 8-FLTMQ Conc, M | n | $pD_2{}^b$ | $\Delta pD_2{}^c$ | $pK_B \pm SEM^d$ |
|---|---|---|---|---|
| None | 16 | 8.17 ± 0.06 | — | — |
| $3 \times 10^{-6}$ | 5 | 7.20 ± 0.12$^e$ | 0.96 ± 0.19 | 6.42 ± 0.22 |
| $1 \times 10^{-5}$ | 4 | 6.81 ± 0.12$^e$ | 1.36 ± 0.12 | 6.60 ± 0.07 |
| $3 \times 10^{-5}$ | 5 | 6.25 ± 0.14$^e$ | 1.92 ± 0.14 | 6.43 ± 0.14 |

$^a$Values are the mean ± SEM of n = 4-16
$^b pD_2 = \text{Log } EC_{50}$
$^c \Delta pD_2 = pD_2$ (control) - $pD_2$ (treatment)
$^d pK_B = -\text{Log } [A]/(CR-1)$ where [A] = molar concentration of analog and CR = concentration ratio = $EC_{50}$ (plus analog)/$EC_{50}$ (control)
$^e p<0.05$ - significantly different from control The antiaggregatory and antisecretory activity on human platelets was determined by evaluating the in vitro aggregation and [$^{14}$C]serotonin secretion in human platelet preparations. Blood was taken by venipuncture from normal human volunteers who were reported to be free of medication for at least 10 days before blood drawing. Venous blood samples were mixed with acid-citrate dextrose solution (9:1) and centrifuged at 120×g for 15 minutes at room temperature to obtain platelet-rich plasma, PRP, (Huzoor-Akbar et al., *Biochem. Pharmacol.*, 30: 2013-2020, 1981). The PRP was transferred to polypropylene tubes and stored under an atmosphere of 8% $CO_2$. The remaining blood was centrifuged at 1000×g for 10 minutes to obtain platelet-poor plasma. Platelets were counted by phase contrast microscopy and the aggregation studies were performed according to the method of Born, *Nature*, (London) 194: 927-929, (1962) as modified by Mustard et al., *Br. J. Haematol.*, 22: 193-204 (1972) using a Payton (Model 600) or Chrono-Log (Model 560) dual channel aggregometer. interfaced to an Apple microcomputer for acquisition, quantitation, presentation and management of platelet aggregation data (Huzoor-Akbar et al., *Thrombosis Res.*, 32: 335-341, 1983). Platelet counts varied between 280,000 to 320,000 per cmm or were adjusted to 300,000 per cmm for the aggregation and secretion experiments. All studies were conducted within 2 hours after PRP recovery.

For aggregation studies, 0.5 ml of PRP was incubated with drug or vehicle (1-5 μl) for 1 minute at 37° C. before the initiation of aggregation with inducers. This time period also served as the incubation interval for trimetoquinol and analogs. In all experiments, the minimum concentration of inducer (adenosine diphosphate ADP; epinephrine, E; 15S-hydroxy-11α,9α-epoxymethanoprosta-5Z,13E-dienoic acid, U46619; collagen; and arachidonic acid, AA) which caused maximal irreversible aggregation within each PRP preparation was used. Aggregation was monitored for 4 to 6 minutes after the addition of an inducer and data were presented as a percentage inhibition of either slope or maximal light transmittance changes in the presence of varying drug concentrations.

Secretion data were calculated as the net increase of serotonin released into the supernatant by each inducer and expressed as a percentage of the total radioactivity in platelets Mayo et al., *Biochem. Pharmacol.*, 30: 2237-2241, 1981. The effect of compounds on serotonin release was expressed as the percentage of inhibition of the maximum release by each inducer and plotted against the log molar concentrations of each agent. The results, as shown in FIGS. 6 to 20, are summarized in the following Tables 5, 6, 7, 8 and 9. Data show that trimetoquinol (1) and trimetoquinol analogs (2 and 3) are inhibitors of aggregation and serotonin release by each inducer in human platelet preparations. The rank order of inhibitory potency for these drugs was 1>3>2 against all of the inducers. In each case, trimetoquinol analog 3 was about 2-fold more potent than 2 as an inhibitor of human platelet activation. Thus, fluorine atom substitution at the 5- or 8-position of the tetrahydroisoquinoline nucleus gave compounds (2 and 3, respectively) that retain significant antithrombotic activities in human platelets.

TABLE 5

Trimetoquinol (TMQ), 8-Fluorotrimetoquinol (8-FLTMQ) and 5-Fluorotrimetoquinol (5-FLTMQ) Mediated Inhibition of Platelet Aggregation and Serotonin Secretion by U46619 [0.5-1.5 μM] in Presence of Aspirin [1 mM] in HUman Platelet-Rich Plasma

| | Platelet Aggregation | | | Serotonin Secretion | | |
|---|---|---|---|---|---|---|
| Compound | $IC_{50}{}^a$ | $pIC_{50}{}^b$ | Potency Ratio$^c$ | $IC_{50}{}^a$ | $pIC_{50}{}^b$ | Potency Ratio$^c$ |
| TMQ | 0.44 (10) | 6.36 ± 0.13 | 1.00 | 0.72 (6) | 6.16 ± 0.23 | 1.00 |
| 8-FLTMQ | 3.9 (6) | 5.41 ± 0.18 | 0.11 | 4.4 (4) | 5.36 ± 0.10 | 0.16 |
| 5-FLTMQ | 7.4 (7) | 5.13 ± 0.11 | 0.06 | 6.9 (6) | 5.16 ± 0.04 | 0.1 |

$^a IC_{50}$ - Inhibitory concentration-50 (μM). Values are the mean ± SEM of n = 4-10 as indicated by the numbers in parentheses.
$^b pIC_{50} = -\text{Log } IC_{50}$
$^c$Potency Ratio = $IC_{50}$ (TMQ)/$IC_{50}$(Drug)

TABLE 6

Trimetoquinol (TMQ), 8-Fluorotrimetoquinol (8-FLTMQ) and 5-Fluorotrimetoquinol (5-FLTMQ) Mediated Inhibition of Platelet Aggregation and Serotonin Secretion by Arachidonic Acid (AA) [100–300 μM] in Human Platelet-Rich Plasma

| Compound | Platelet Aggregation | | | Serotonin Secretion | | |
|---|---|---|---|---|---|---|
| | $IC_{50}$ (μM)[a] | $pIC_{50}$[b] | Potency Ratio[c] | $IC_{50}$ (μM)[a] | $pIC_{50}$[b] | Potency Ratio[c] |
| TMQ | 1.04 (7) | 5.98 ± 0.21 | 1.00 | 1.33 (8) | 5.90 ± 0.16 | 1.00 |
| 8-FLTMQ | 26.2 (7) | 4.58 ± 0.13 | 0.04 | 21.9 (8) | 4.66 ± 0.13 | 0.06 |
| 5-FLTMQ | 77.5 (5) | 4.11 ± 0.21 | 0.014 | 55 (6) | 4.26 ± 0.24 | 0.023 |

[a]$IC_{50}$ = Inhibiting concentration-50. Values are the mean ± SEM of n = 5–8 as indicated by the numbers in parentheses.
[b]$pIC_{50}$ = −Log $IC_{50}$
[c]Potency Ratio = $IC_{50}$ (TMQ)/$IC_{50}$ (Drug)

TABLE 7

Trimetoquinol (TMQ), Fluorotrimetoquinol (8-FLTMQ) and 5-Fluorotrimetoquinol (5-FLTMQ) Mediated Inhibition of Platelet Aggregation and Serotonin Secretion by Collagen [10–100 μg/ml] in Human Platelet-Rich Plasma

| Compound | Platelet Aggregation | | | Serotonin Secretion | | |
|---|---|---|---|---|---|---|
| | $IC_{50}$ (μM)[a] | $pIC_{50}$[b] | Potency Ratio[c] | $IC_{50}$ (μM)[a] | $pIC_{50}$[b] | Potency Ratio[c] |
| TMQ | 0.93 (4) | 6.03 ± 0.14 | 1.00 | 0.62 (4) | 6.23 ± 0.24 | 1.00 |
| 8-FLTMQ | 9.8 (5) | 5.01 ± 0.1 | 0.096 | 7.5 (4) | 5.12 ± 0.17 | 0.078 |
| 5-FLTMQ | 51.3 (8) | 4.29 ± 0.09 | 0.018 | 13.2 (4) | 4.88 ± 0.04 | 0.045 |

[a]$IC_{50}$ = Inhibitory concentration-50. Values are the mean ± SEM of n = 4–8 as indicated by the numbers in parentheses.
[b]$pIC_{50}$ = −Log $IC_{50}$
[c]Potency Ratio = $IC_{50}$ (TMQ)/$IC_{50}$ (Drug)

TABLE 8

Trimetoquinol (TMQ), 8-Fluorotrimetoquinol (8-FLTMQ) and 5-Fluorotrimetoquinol (5-FLTMQ) Mediated Inhibition of the Secondary Phase of Platelet Aggregation and of Serotonin Secretion by ADP [1–3 μM] in Human Platelet-Rich Plasma

| Compound | Platelet Aggregation | | | Serotonin Secretion | | |
|---|---|---|---|---|---|---|
| | $IC_{50}$ (μM)[a] | $pIC_{50}$[b] | Potency Ratio[c] | $IC_{50}$ (μM)[a] | $pIC_{50}$[b] | Potency Ratio[c] |
| TMQ | 0.34 (6) | 6.57 ± 0.22 | 1.00 | 0.23 (7) | 6.70 ± 0.30 | 1.00 |
| 8-FLTMQ | 6.5 (5) | 5.19 ± 0.19 | 0.042 | 6.6 (6) | 5.18 ± 0.11 | 0.030 |
| 5-FLTMQ | 15.1 (4) | 4.82 ± 0.23 | 0.018 | 17.0 (6) | 4.77 ± 0.18 | 0.012 |

[a]$IC_{50}$ = Inhibitory concentration-50. Values are the mean ± SEM of n = 4–7 as indicated by the numbers in parentheses.
[b]$pIC_{50}$ = −Log $IC_{50}$
[c]Potency Ratio = $IC_{50}$ (TMQ)/$IC_{50}$ (Drug)

TABLE 9

Trimetoquinol (TMQ), 8-Fluorotrimetoquinol (8-FLTMQ) and 5-Fluorotrimetoquinol (5-FLTMQ) Mediated Inhibition of the Secondary Phase of Platelet Aggregation and of Serotonin Secretion by Epinephrine [1–10 μM] in Human Platelet-Rich Plasma

| Compound | Platelet Aggregation | | | Serotonin Secretion | | |
|---|---|---|---|---|---|---|
| | $IC_{50}$ (μM)[a] | $pIC_{50}$[b] | Potency Ratio[c] | $IC_{50}$ (μM)[a] | $pIC_{50}$[b] | Potency Ratio[c] |
| TMQ | 1.73 (10) | 5.78 ± 0.13 | 1.00 | 1.15 (4) | 5.99 ± 0.34 | 1.00 |
| 8-FLTMQ | 11.0 (8) | 4.96 ± 0.22 | 0.15 | 3.5 (5) | 5.46 ± 0.24 | 0.30 |
| 5-FLTMQ | 14.8 (11) | 4.83 ± 0.16 | 0.11 | 7.4 (5) | 5.12 ± 0.09 | 0.14 |

[a]$IC_{50}$ = Inhibitory concentration-50. Values are the mean ± SEM of n = 4–7 as indicated by the numbers in parentheses.
[b]$pIC_{50}$ = −Log $IC_{50}$
[c]Potency Ratio = $IC_{50}$ (TMQ)/$IC_{50}$ (Drug)

The following examples illustrate the present invention. Melting points were taken on a Thomas-Hoover melting point apparatus and are uncorrected. Infrared data were collected on a Beckman 4230 spectrophotometer. The $^1$H NMR were recorded on a Bruker HX-90E or an IBM 270 spectrometer with tetramethylsilane as the internal standard. The mass spectra were obtained at The Ohio State University Chemical Instrument Center, by use of a Kratos MS-30 mass spectrometer. Chemical analyses were determined by Galbraith Laboratories, Inc., Knoxville, TN and all were found to be within ±0.4% of theoretical values. TLC was performed on silica gel 60 F precoated aluminum-backed plates from EM reagents. Column chromatography was performed on silica 60, 70–230 mesh, from EM Reagents. Flash chromatography was performed on flash silica gel 60, 40–240 mesh, from EM Reagents. All reagents were dried prior to use.

The following abbreviations are used:
MeOH-methylalcohol
EtOH-ethylalcohol
Et$_2$O-diethylether
DMSO-dimethylsufoxide
DMK-acetone
THF-tetrahydrofuran
Pd/C-palladium on charcoal

EXAMPLE I

N,N-Dimethyl-(3-methoxy-4-hydroxy-5-fluoro)benzylamine (14). 2-Fluoro-6-methoxyphenol 13 (10 g, 76 mmol) was added to a solution of 40% aqueous dimethylamine (24 g) and 37% aqueous formaldehyde (9 mL) in absolute EtOH (20 mL). The mixture was heated at reflux for 2 h, cooled and concentrated under reduced pressure to give a solid, which was crystallized from Et$_2$O to yield 13.5 g (95%) of 14 as colorless needles: mp 140°–142° C.; IR(KBr) 3400 cm$^{-1}$, $^1$H NMR δ 6.71–6.58 (m, 2H, Ar—H), 3.83 (s, 3H, ArOCH$_3$), 3.33 (s, 2H, ArCH$_2$N), 2.23 (s, 6H, N(CH$_3$)$_2$); analysis calc. for C$_{10}$H$_{14}$FNO$_2$; C, H, N.

EXAMPLE II

3-Methoxy-4-hydroxy-5-fluorobenzylnitrile (15). Iodomethane (12 mL) was added to a solution of N,N-dimethyl-(3-methoxy-4-hydroxy-5-fluoro)benzylamine (14, 5 g, 25 mmol) in CHCl$_3$ (100 mL). The mixture was stirred for 18 h at 25° C. The precipitate that formed was collected to give 8.9 g of a white solid. Without further purification, the white solid was dissolved in DMSO (50 mL) and NaCN (2.25 g, 46 mmol) was added. The mixture was stirred for 7 h at 25° C. The mixture was added to H$_2$O (25 mL) and acidified with 6N HCl. The solution was extracted with EtOAc (3×50 mL), the EtOAc extracts washed with brine (2×150 mL), dried with anhydrous MgSO$_4$ and concentrated under reduced pressure to give a solid. The solid was crystallized from EtOAc/hexanes to 2.42 g (58%) of 15 as light yellow needles: mp 70°–80° C.; IR (KBr) 3200 cm$^{-1}$, 2400 cm$^{-1}$; $^1$H NMR (CDCl$_3$) δ 6.76–6.64 (m, 2H, Ar—H), 5.43 (b, 1H, ArOH), 3.92 (s, 3H, ArOCH$_3$), 3.66 (s, 2H, ArCH$_2$CN); analysis calc. for C$_9$H$_8$FNO$_2$; C, H, N.

EXAMPLE III 3,4-Dihydroxy-5-fluorobenzylcyanide (16). Boron tribromide (1.03 mL, 11 mmol) was added dropwise to a cool (0° C.) solution of 3-methoxy-4-hydroxy-5-fluorobenzylnitrile (15, 1 g, 5.5 mmol) in CH$_2$Cl$_2$ (10 mL). The mixture was warmed to 25° C. and stirred at that temperature for 18 h. The mixture was concentrated under reduced pressure to give a solid. The solid was dissolved in EtOAc (50 mL), washed with brine (3×50 mL), H$_2$O (3×5 mL), dried (MgSO$_4$) and concentrated under reduced pressure to give a solid. The solid was crystallized from EtOAc/Et$_2$O to give 900 mg (90.1%) of 16 as a white solid; mp 100°–101° C.; IR (KBr) 3400 cm$^{-1}$, 2400 cm$^{-1}$; $^1$H NMR (CDCl) δ 6.60–6.646 (m, 2H, ArH), 3.72 (s, 2H, ArCH$_2$CN); analysis calc. for C$_8$H$_6$FNO$_2$: C, H, N.

EXAMPLE IV 3,4-Dibenzyloxy-5-fluorobenzylcyanide (12). Benzyl chloride (0.54 mL), 4.5 mmol) was added to a solution of 3,4-dihydroxy-5-fluorobenzylcyanide 16 (330 mg, 2 mmol), K$_2$CO$_3$ (620 mg, 4.5 mmol) and KI (50 mg) in DMK (10 mL). The mixture was heated at reflux for 4 h, cooled and concentrated under reduced pressure. The residue was dissolved in H$_2$O (10 mL), and EtOAc (10 mL). The organic layer was washed with brine (2×10 mL), H$_2$O (2×10 mL), dried with anhydrous MgSO$_4$ and concentrated under reduced pressure to an oil. The oil was purified by flash chromatography (20% EtOAc/hexanes) to give an oil which solidified on standing. The solid was crystallized from CH$_2$Cl$_2$/hexanes to give 555 mg (80%) of 12 as white needles: mp 120°–121° C.; IR (KBr) 2400 cm$^{-1}$; $^1$H NMR (CDCl$_3$) δ 7.47–7.25 (m, 10H, ArH), 6.76–6.61 (m, 2H, ArH), 5.11 (s, 4H, ArCH$_2$), 3.63 (s, 2H, ArCH$_2$CN); analysis calc. for C$_{22}$H$_{18}$FNO$_2$; C, H, N.

EXAMPLE V

General Synthesis of the Phenylethylamines 4 and 5. To a cold solution (0° C.) of the benzylcyanides 11 or 12 (2 g, 5.8 mmol) in dry THF (30 mL) was added dropwise a 1M BH$_3$-THF solution (100 mL, 100 mmol). The mixture was heated at reflux for 18 h, cooled to 0° C. and MeOH (15 mL) was added cautiously. The mixture was concentrated under reduced pressure to an oil. The oil was dissolved in MeOH (15 mL) and reconcentrated under reduced pressure (this was repeated 2 more times) to give an oil. The oil was dissolved in Et$_2$O (30 mL) washed with 10% NaHCO$_3$ (3×30 mL), H$_2$O (3×30 mL), dried with anhydrous MgSO$_4$ and concentrated under reduced pressure to give an oil. The oil was dissolved in MeOH (20 mL) and HCl gas was added to the solution. Diethyl ether was added until the solution became cloudy and a solid crystallized from the solution. The solid was collected to give 4 or 5 as their hydrochloride salts.

Compound 4.HCl (85%); mp 111°–113° C.; NMR (CDCl$_3$), free base δ 7.43–7.25 (m, 10H, Ar—H), 6.90–6.60 (m, 2H, Ar—H), 5.10 (s, 4H, ArCH$_2$O), 2.90–2.60 (m, 4H, CH$_2$), 1.26 (s, 2H, NH$_2$); analysis calc. for C$_{22}$H$_{23}$ClFNO$_2$; C, H, N.

Compound 5.HCl (90%); mp 128°–130° C.; NMR (CDCl$_3$), free base δ 7.44–7.25 (m, 10H, ArH), 6.53–6.39 (m, 2H, ArH), 5.05 (s, 2H, ArCH$_2$O), 5.03 (s, 2H, ArCH$_2$O), 3.2–2.9 (m, 4H, CH$_2$); analysis calc. for C$_{22}$H$_{23}$ClFNO$_2$.½H$_2$O; C, H, N.

EXAMPLE VI

General Synthesis of Phenylacetamides 7 and 8. The hydrochloride salts of 4 and 5 (2.2 g, 5.6 mmol) were dissolved in CH$_2$Cl$_2$ (50 mL) and washed with a 10% NaHCO$_3$ solution (3×50 mL), H$_2$O (3×50 mL), dried with anhydrous MgSO$_4$ and concentrated under reduced pressure to give the free bases as oils. The oil was dissolved in toluene (50 mL) and 3,4,5-trimethylphenylacetic acid (1.29 g, 5.6 mmol) was added. The mixture was heated at reflux for 72 h with removal of H$_2$O via a Dean Stark trap. The mixture was cooled and concentrated under reduced pressure to give a solid. The solid was dissolved in CH$_2$Cl$_2$ (50 mL) and washed with H$_2$O (50 mL), 10% HCl (2×50 mL), H$_2$O (50 mL), 10% NaHCO$_3$ (2×50 mL) and H$_2$O (2×50 mL), dried with anhydrous MgSO$_4$ and concentrated under reduced pressure to give a solid. The solid was crystallized from EtOAc to give 7 or 8 as white solid.

Compound 7 (75%); mp 109°–111° C.; NMR (CDCl$_3$) δ 7.54–7.29 (m, 10H, Ar—H), 6.62–6.57 (m, 2H, Ar—H), 6.39 (s, 2H, Ar—H) 5.54–5.35 (br, 1H, NH), 5.10–5.07 (s, 4H, 2xArCH$_2$O), 3.86 (s, 3H, Ar—OCH$_3$), 3.80 (s, 6H, 2xAr—OCH$_3$), 3.56–3.32 (m, 4H, Ar—CH$_2$C), 2.79–2.64 (t, 2H, CH$_2$—N); analysis calc. for C$_{33}$H$_{34}$FNO$_6$; C, H, N.

Compound 8 (75%); mp 94°–95° C.; NMR (CDCl$_3$) δ 7.44–7.24 (m, 10H, Ar—H), 6.53–6.39 (m, 4H, Ar—H), 5.45 (b, 1H, NH), 5.06 (s, 4H, 2xAr—CH$_2$), 3.83 (s, 9H, ArOCH$_3$), 3.55 (s, 2H, COCH$_2$Ar), 3.44 (m, 2H, Ar—CH$_2$C), 2.65 (t, 2H, CH$_2$—N); analysis calc. for C$_{33}$H$_{34}$FNO$_6$; C, H, N.

EXAMPLE VII

General Synthesis of the Protected 1,2,3,4-Tetrahydroisoquinolines 9 and 10. Phosphorous oxychloride (0.83 mL, 9 mmol) was added to the phenylacetamides 7 or 8 (2 g, 3.6 mmol) in PhCH$_3$ (24 mL). The mixture was heated at 80° C. for 5 h under argon atmosphere. The mixture was cooled and concentrated under reduced pressure to give an oil. The oil was dissolved in EtOH (100 mL) and cooled to 0° C. where upon NaBH₄ (4.24 g, 11.2 mmol) was added. The mixture was stirred for 18 h at 25° C. and concentrated under reduced pressure to a solid. The solid was dissolved in H₂O (50 mL) and 10% NaOH (10 mL) was added. The mixture was extracted with Et₂O (2×50 mL), the organic layer was washed with H₂O (2×50 mL), dried with anhydrous MgSO₄ and concentrated to an oil. The oil was purified by flash chromatography (5% MeOH/CH₂Cl₂) to give clear oils that were converted to HCl salts 9 and 10.

Compound 9 (25%); mp 125°–127° C.; NMR (CDCl₃), free base δ 7.43–7.26 (m, 10H, ArH), 6.39 (s, 2H, ArH), 6.11 (d, 1H, ArH, $J_{HF}$=1.3 Hz), 5.07 (s, 2H, ArCH₂), 4.79 (q, 2H, ArCH₂), 4.69 (m, 1H, ArCHNH), 3.81 (s, 3H, ArOCH₃), 3.75 (s, 8H, ArOCH₃), 3.52–2.98 (m, 6H, CH₂); analysis calc. for $C_{33}H_{35}ClFNO_5$; C, H, N.

Compound 10 (65%); mp 179°–181° C.; NMR (CDCl₃), free base δ 7.48–7.26 (m, 10H, ArH), 6.84 (d, 1H, ArH) 6.51 (s, 2H, ArH), 5.16 (s, 2H, ArCH₂), 5.02 (s, 2H, ArCH₂) 4.95 (m, 1H, ArCHNH), 3.78 (s, 6H, ArOCH₃), 3.72 (s, 3H, ArOCH₃), 3.56–3.05 (m, 6H, CH₂); analysis calc. for $C_{33}H_{35}ClFNO_5 \cdot 3H_2O$; C, H, N.

EXAMPLE VIII

General Synthesis of the 1,2,3,4-Tetrahydroisoquinolines 2 and 3. The protected 1,2,3,4-tetrahydroisoquinolines 9 or 10 was dissolved in Et₂O and HCl gas was added to give the hydrochloride salts of 9 and 10. The hydrochloride salts were dissolved in EtOH and added to a suspension of 10% Pd/C in EtOH. The mixture was hydrogenated for 8 h at 45 psi at 25° C. The mixture was filtered and concentrated under reduced pressure to give an oil which solidified upon standing. The oil was crystallized from MeOH/Et₂O or MeOH/CH₂Cl₂ to give 2 or 3 as white solids.

Compound 2 (65%); mp 165°–169° C.; NMR (CD₃OH) δ 6.63 (s, 2H, ArH), 6.50 (d, 1H, ArH, $J_{HF}$=0.9 Hz), 3.83 (s, 6H, ArOCH₃), 3.76 (s, 3H, ArOCH₃), 3.60–2.90 (m, 7H, CH₂CH); analysis calc. for $C_{19}H_{23}ClFNO_5 \cdot 2\frac{1}{2}H_2O$; C, H, N.

Compound 3 (65%); mp 219°–221° C.; NMR (CD₃OH) δ 6.56 (s, 2H, ArH), 6.51 (d, 1H, Arh, $J_{HF}$=0.8 Hz), 3.81 (s, 6H, ArOCH₃), 3.75 (s, 3H, ArOCH₃), 3.40–2.93 (m, 7H, CH₂CH); analysis calc. for $C_{19}H_{23}ClFNO_5 \cdot \frac{1}{2}H_2O$; C, H, N.

We claim:

1. A trimetoquinol compound selected from the group consisting of compounds of the formula I:

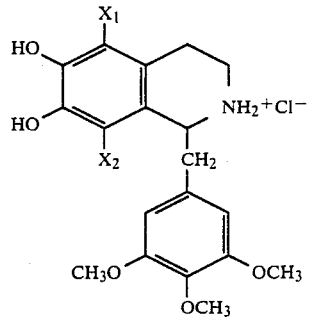

wherein $X_1$ is fluorine, $X_2$ is hydrogen or $X_1$ is hydrogen, $X_2$ is fluorine, and physiologically acceptable salts thereof.

2. 5-Fluoro-1,2,3,4-tetrahydroisoquinoline and its physiologically acceptable salts.

3. 8-Fluoro-1,2,3,4-tetrahydroisoquinoline and its physiologically acceptable salts.

4. A compound according to claim 1, wherein the physiologically acceptable salt is selected from the group consisting of hydrochloride, hydrobromide, phosphate, sulphate, citrate, tartrate, acetate, maleate and succinate.

5. A β₂-adrenoreceptor agonist composition comprising a compound selected from the group consisting of compounds of formula I of claim 1, physiologically acceptable salts thereof and their mixtures together with a physiologically acceptable carrier or excipient.

6. A pharmaceutical composition having β₂-adrenergic activity which comprises, as active ingredient, a compound of formula I of claim 1, in association with a pharmaceutically acceptable carrier.

7. A method for increasing the β₂-adrenergic activity in a subject in need thereof while simultaneously decreasing the β₁-adrenergic activity in said subject which comprises administering parenterally or by insufflation to said subject a non-toxic, effective quantity of a compound of formula 1 of claim 1 combined with a suitable pharmaceutical carrier or excipient.

8. The method of claim 7 in which the increase in β₂-adrenergic activity is manifest as a bronchodilating effect.

9. The method of claim 7 in which the increase in antithromboxane A₂ activity is manifest as a reduced or inhibited vasoconstrictive effect.

10. The method of claim 7 in which the increase in antithrombotic activity is manifest as a reduced or inhibited blood platelet aggregatory effect.

* * * * *